(12) United States Patent
Bonner, Jr. et al.

(10) Patent No.: US 6,197,776 B1
(45) Date of Patent: Mar. 6, 2001

(54) METHOD FOR TREATMENT OF REACTIVE ARTHRITIS OR BURSITIS

(76) Inventors: Ernest L. Bonner, Jr., 1406 Park St., Suite 400, Alameda, CA (US) 94501; Robert Hines, 3637 Cape Center Dr., Fayetteville, NC (US) 28304

( * ) Notice: Subject to any disclaimer, the term of this patent is extended or adjusted under 35 U.S.C. 154(b) by 0 days.

(21) Appl. No.: 09/613,876

(22) Filed: Jul. 10, 2000

Related U.S. Application Data

(63) Continuation-in-part of application No. 09/270,962, filed on Mar. 17, 1999, now Pat. No. 6,087,382, and a continuation-in-part of application No. 09/510,704, filed on Feb. 22, 2000.

(51) Int. Cl.[7] .......................... A61K 31/52; A61K 31/44; A61K 31/415; A61K 31/195
(52) U.S. Cl. .......................... 514/262; 514/356; 514/398; 514/561
(58) Field of Search ...................................... 514/262, 356, 514/398, 561

(56) References Cited

U.S. PATENT DOCUMENTS

| | | | | |
|---|---|---|---|---|
| 2,946,801 | * | 7/1960 | Fields ..................................... | 260/295 |
| 3,148,212 | * | 9/1964 | Boothe et al. ........................ | 260/559 |
| 3,226,436 | * | 12/1965 | Petisi et al. .......................... | 260/559 |
| 5,523,297 | * | 6/1996 | Pruzanski et al. ................... | 514/152 |

* cited by examiner

*Primary Examiner*—Raymond Henley, III
(74) *Attorney, Agent, or Firm*—Brian Beverly

(57) ABSTRACT

An improved method for treatment of conditions in human beings associated with either or both reactive arthritis or bursitis comprising administration of a combination of acyclovir, L-lysine, minocycline hydrochloride, and metronidazole. An alternate method comprises administration of isonicotinic acid hydrazide.

50 Claims, No Drawings

METHOD FOR TREATMENT OF REACTIVE ARTHRITIS OR BURSITIS

This is a continuation-in-part of application Ser. No. 09/270,962, filed Mar. 17, 1999, now U.S. Pat. No. 6,087,382, and of application Ser. No. 09/510,704, filed Feb. 22, 2000, and which is still pending.

BACKGROUND OF THE INVENTION

This invention relates to an improved treatment for symptoms associated in humans with reactive arthritis or idiopathic bursitis.

Reactive arthritis refers to a spondyloarthritity which usually arises as a complication of an infection elsewhere in the body. Reactive arthritis can be caused by species of Shigella bacteria (most notably *Shigella flexneri*), *Yersinia enterocolitica, Campylobacter jejuni*, several species of Salmonella, genitourinary pathogens, *Chlamydia trachomatis, Neisseria gonorrhea, Ureaplasma urealyticum, Streptococcus pyogenes*, and other yet unidentified infectious agents.

Reactive arthritis commonly occurs in young men and women, but can occur at any age. Sufferers experience joint pain, stiffness, redness or swelling. Common symptoms may include fatigue, malaise, fever, and weight loss. The joints of the lower extremities, including the knee, ankle, and joints of the foot, are the most common sites of involvement, but symptoms can also occur in the wrists, fingers, elbows, shoulders, neck, and lower back. Other symptoms may include urethritis and prostatitis in males, and cervicitis or salpingitis in females. Ocular disease is common ranging from transient, asymptomatic conjunctivitis to aggressive anterior uveitis that occasionally results in blindness. Mucocutaneous lesions and nail changes are frequent. On less frequent or rare occasions manifestations of reactive arthritis include cardiac conduction defects, aortic insufficiency, central or peripheral nervous system lesions, and pleuropulmonary infiltrates.

Treatment of patients suffering from reactive arthritis with nonsteroidal anti-inflammatory drugs ("NSAID") provides some benefit, although symptoms of reactive arthritis are rarely completely alleviated and some patients fail to respond at all. The preferred initial treatment of choice for acute reactive arthritis is indomethacin in divided doses of 75 to 150 milligrams per day. The NSAID of last resort is phenylbutazone, in doses of 100 milligrams twice or three times per day, because of its potentially serious side effects. Patients with debilitating symptoms refractory to NSAID therapy may be treated with cytotoxic agents such as azathioprine or methotrexate, or with sulfasalazine. Tendinitis, other lesions, and uveitis may benefit from corticosteroids. Minocycline hydrochloride, a semisynthetic derivative of tetracycline, is indicated for infections caused by at least Shigella microorganisms, *Streptococcus pyogenes*, and *Neisserie gonorrhoeae*. It is therefore an accepted treatment in incidents of reactive arthritis triggered by these biological entities.

Long-term follow-up studies have suggested that some joint symptoms persist in many, if not most, patients with reactive arthritis. Recurrences of the more acute symptoms are common and as many as twenty-five percent of patients either become unable to work or are forced to change occupations because of persistent joint problems.

Bursitis is inflammation of a bursa, a thin-walled sac lined with synovial tissue. The function of the bursa is to facilitate movement of tendons and muscles over bony prominences. Bursitis may be caused by excessive frictional forces, trauma, systemic disease such as rheumatoid arthritis or gout, or infection. The most common form of bursitis is subacromial. Trochanteric bursitis causes patients to experience pain over the lateral aspect of the hip and upper thigh, and tenderness over the posterior aspect of the greater trochanter. Retrocalcaneal bursitis involves the bursa located between the calcaneus and the posterior surface of the Achilles tendon. Pain is experienced at the back of the heel, and swelling appears on either or both of the medial and lateral sides of the tendon. Retrocalcaneal bursitis occurs in association with spondyloarthritities, rheumatoid arthritis, gout, and trauma.

Treatment of bursitis generally consists of prevention of the aggravating condition, rest of the involved part, an NSAID, and local steroid injection. In the long term, bursitis can result in loss of use of a joint and chronic pain syndrome.

The long term effects of reactive arthritis and bursitis range from chronic pain to crippling disability. It is also thought that many instances of osteoarthritis and psoriatic arthritis are in actuality reactive arthritis. Unfortunately, current procedures for management treat the symptoms of these diseases rather than their underlying pathogens.

SUMMARY OF THE INVENTION

The inventors have discovered that significant benefits can be obtained by treating humans affected with conditions associated with reactive arthritis or bursitis using combinations of acyclovir, L-lysine, minocycline hydrochloride, and metronidazole. An alternate embodiment of the invention involves the addition of isonicotinic acid hydrazide (commonly referred to as InH) to the above combination.

Acyclovir is an anti-viral drug. The chemical name of acyclovir is 2-amino-1,9-dihydro-9-[(2-hydroxyethoxy) methyl]-6H-purin-6-one. Acyclovir is commercially available under the brand name ZOVIRAX® in capsules, tablets, or suspension. Acyclovir has demonstrated anti-viral activity against herpes simplex virus types I and II, varicella-zoster virus, Epstein-Barr virus and cytomegalovirus, both in vitro and in vivo.

L-lysine has been shown to inhibit the growth of herpes virus cultures and can be effective in alleviating the symptoms associated with herpes infections, both oral and genital.

Minocycline hydrochloride is a bacteriostatic antibiotic which exerts its antimicrobial effect by inhibition of bacterial protein synthesis. It has been shown to be effective against gram-negative bacteria, some gram-positive bacteria and other microorganisms.

Metronidazole is an oral synthetic antiprotozoal and antibacterial agent. Heretofore it has been indicated for treatment of symptomatic trichomoniasis, intestinal amebiasis, and a wide range of intra-abdominal, skin, and gynecological, bone and joint, and lower respiratory tract and central nervous system infections, bacterial septicemia and endocarditis.

InH is known to act against actively growing tubercle bacilli. Heretofore, InH has been indicated for treatment of pulmonary tuberculosis. Adults with high doses of InH sometimes are observed to have a deficiency of pyridoxine hydrochloride. Appropriate doses of pyridoxine hydrochloride are therefore administered to patients being treated with InH.

A beneficial method for treatment of the symptoms in human beings of reactive arthritis or idiopathic bursitis, or both, comprises the administration of the combination of L-lysine, minocycline hydrochloride, and metronidazole. The preferred method includes administration of acyclovir with the underlying combination of L-lysine, minocycline hydrochloride, and metronidazole. An alternative method includes the administration of InH.

The method of treatment of the invention puts the diseases of reactive arthritis and bursitis into remission. The treatment may effect a cure of reactive arthritis and bursitis, but definitive testing has not been performed to confirm that fact.

It is therefore a primary object of the invention to provide a method of treatment for conditions in human beings associated with either or both reactive arthritis or idiopathic bursitis.

Another object of the invention is to provide a method of treatment for conditions in human beings associated with either or both reactive arthritis or idiopathic bursitis that puts the disease being treated into full remission.

A further object of the invention is to provide a method of treatment for any constellation of symptoms amenable to treatment using the above combination, including for example, cases of reactive arthritis which have been misdiagnosed as osteoarthritis or psoriatic arthritis.

DETAILED DESCRIPTION OF THE INVENTION

The method of treatment described in application Ser. No. 09/270,962 involves administration of a combination of L-lysine, minocycline hydrochloride, and metronidazole. An alternate method includes administration of InH for those individuals who have tested positively for mycobacterial exposure, along with the underlying combination of L-lysine, minocycline hydrochloride, and metronidazole. Another method described in application Ser. No. 09/510,704 includes administration of valacyclovir hydrochloride with the underlying combination of L-lysine, minocycline hydrochloride, and metronidazole. The preferred embodiment of the present treatment method comprises administration of acyclovir with the underlying combination of L-lysine, minocycline hydrochloride, and metronidazole. Any of these embodiments may be supplemented with administration of pyridoxine hydrochloride, glucosamine, manganese, vitamin C, and desalinated seawater, such as Essence of Life.

Administration will generally be accomplished orally, but delivery could be accomplished by injection, or any other method commonly used for administration of internal medicines.

L-lysine inhibits the growth of herpes simplex viruses. The preferred dosage of L-lysine is 2 grams daily. The daily dose of L-lysine may vary from 1 to 10 grams.

The preferred dose of minocycline hydrochloride is an initial dosage of 200 mg followed by doses of 100 mg twice per day. Daily doses of minocycline hydrochloride following the initial administration of 200 mg may vary from 50 mg to 200 mg.

The preferred dose of metronidazole is 250 mg four times per day. The total dose per day of metronidazole may vary from 100 mg to 1,000 mg.

The preferred dose of InH in an adult is 300 mg per day and is usually reserved for those individuals who have tested positively for mycobacterial exposure. Accordingly, InH is administered only in those individuals for whom it is indicated. The daily dose of InH may vary from 50 mg to 300 mg.

Acyclovir also inhibits herpes simplex viruses, but while L-lysine tends to stop the virus from replicating by inhibiting the initiation of the replication process, acyclovir inhibits effective replication of actively replicating viral particles by stopping replication of herpes viral DNA. This is accomplished by either competitive inhibition or inactivation of viral DNA polymerase or incorporation and termination of the growing viral DNA chain. Acyclovir has never been used in the prior art for treatment of arthritis or bursitis. It does not appear to be effective alone for the treatment of these diseases. The daily dose of acyclovir may vary from 200 mg to 4 grams. The preferred dose of acyclovir is 400 mg twice daily.

The combination of minocycline hydrochloride, InH, and metronidazole inhibits the multiplication of susceptible organisms, including shigella, salmonella, chlamydia, streptococci, and mycobacteria.

The underlying treatment method involves the underlying combination of L-lysine, minocycline hydrochloride, and metronidazole. Where affected individuals have tested positively for mycobacterial exposure, the treatment method includes InH in the total combination of medicines administered. The preferred embodiment of the treatment method comprises the combination of acyclovir, L-lysine, minocycline hydrochloride, and metronidazole. It is believed that the addition of acyclovir results in a substantial benefit due to its inhibition of virus replication. The total combination of medicines in each of these embodiments presents a broad spectrum approach that it is believed effectively addresses the underlying pathogenesis for reactive arthritis and what has previously been referred to as idiopathic bursitis, and further is a beneficial treatment for reactive arthritis in particular cases wherein the symptom complex has been misdiagnosed as osteoarthritis or psoriatic arthritis, or in any other similar cases of misdiagnosis.

EXAMPLES

The following examples serve to illustrate the invention, but are not meant to restrict the effective scope of the invention.

Example 1

An adult male presented with symptoms involving his knees, ankles, elbows, wrist and carpophalengeal joints. Stooping activities caused severe pain in his knees. Simple driving activities caused pain in his elbows, wrists, and knees. He was unable to run or jog because of pain in his knees and ankles. Lifting objects weighing more than five pounds caused wrist and hand pain. The patient was treated with metronidazole and minocycline hydrochloride for thirty days and simultaneously with L-lysine and InH for one year. Positive symptomatic relief was achieved within two weeks of treatment with the combination of metronidazole, minocycline hydrochloride, InH, and L-lysine, with complete recovery at the end of the course of treatment with InH. The patient has continued taking L-lysine because of the probable ideologic role of herpes simplex and its tendency to remain present in a dormant state. The patient now has no problems lifting, running or driving. However, it should be kept in mind that infections can reoccur and treatment with at least minocycline hydrochloride and metronidazole may be necessary again.

Example 2

A seventy-one year old female suffered from reactive arthritis and had symptoms of joint pain and stiffness involving her knees, wrists, elbows, and hips. Pain in multiple joints caused difficulty walking, arising from a sitting position to a standing position, and sitting down from a standing position. The patient was unable to run or jog. The patient was treated with metronidazole and minocycline hydrochloride for thirty days and simultaneously with L-lysine and InH for one year. Treatment effected resolution of all joint pains. After treatment the patient was able to walk without pain, to arise from a sitting position, and to sit down from a standing position without difficulty. This patient was also able to jog without discomfort or difficulty.

No adverse side effects have been observed as a result of or during the above described treatments. In the cases tested, the treatment resulted in a dramatic elimination of symptoms of the disease being addressed.

Applicants have determined that, with the contemporaneous administration of valacyclovir hydrochloride in addition to the underlying combination as above of L-lysine, minocycline hydrochloride, and metronidazole, arthritic patients experience substantial beneficial effects. Patients treated with the combination including valacyclovir hydrochloride were found to experience a reduction in pain and stiffness in their affected joints within approximately 48 hours, a substantially quicker response time than patients treated without valacyclovir hydrochloride included in the above combination. Further, while patients being treated with the underlying combination of L-lysine, minocycline hydrochloride, and metronidazole experienced definite beneficial effects as discussed above, some individuals were found to have residual stiffness and pain in joints, though certainly to a lesser degree than before administration of the initial combination. Patients treated with the combination including valacyclovir hydrochloride were shown to have a higher percentage of total resolution of joint stiffness and joint pain. While treatment with the combination including valacyclovir hydrochloride has been shown remarkably effective at resolution of symptoms, definitive tests have not been performed to determine if the combination effects a cure.

Individuals with severe symptoms, including joint swelling and joint contractures, who were not thought to be candidates for treatment using the combination of L-lysine, minocycline hydrochloride, and metronidazole only, have responded to treatment with the underlying combination and valacyclovir hydrochloride.

Example 3

A 46-year-old male initially presented with severe symptoms of reactive arthritis, including joint swelling and joint contractures. His symptoms had previously been diagnosed as psoriatic arthritis. His joint symptoms included pain and stiffness of multiple joints for at least five years. This individual had sausage-shaped digits on his hands and early flexion contractures at the PIP joint of those digits bilaterally. When this patient was seen initially, he had difficulty twisting lids on containers with his hands, grasping small objects, and with prolonged reaching above his head. He was also unable to run, jog, or jump. This patient was treated with a combination of L-lysine, minocycline hydrochloride, metronidazole, and valacyclovir hydrochloride. He noted a significant decrease in his pain and stiffness within 48 hours. Within one week, the joint deformities of the digits of his hands had resolved. After two weeks of treatment, he was able to run, jog, and jump. His grasping abilities significantly improved, and after one month he was able to return to work as a machinist.

Example 4

A 75-year-old female was seen with reactive arthritis previously diagnosed as osteoarthritis. Her joint problems included pain and stiffness in her shoulders, elbows, hips, hands and heels. Multiple joint pains caused her to experience difficulty walking and standing. She was initially placed on L-lysine, minocycline hydrochloride, and metronidazole. Treatment with his combination effected only minimal and transient improvement in her condition. Several months later, she returned in a semi-ambulatory state, being able to ambulate only with a walker—needing assistance to walk even with the walker. She had extreme difficulty standing from a sitting position or sitting from a standing position. She was then started on L-lysine, minocycline hydrochloride, metronidazole, and valacyclovir hydrochloride. Within 48 hours, she noted much less stiffness and much less pain in her joints. Within one month, she was able to ambulate without a walker and she noted resolution of all joint pains excepting occasional intermittent pain in her lower back.

Example 5

A 28-year-old male with reactive arthritis presented with complaints of multiple joint pain and stiffness. His symptoms caused him difficulty in raising his arms above his head, driving and bending over. Treatment was commenced with the combination of L-lysine, minocycline hydrochloride, metronidazole, and valacyclovir hydrochloride. Within 48 to 72 hours, this patient experienced significant diminution in his joint pain severity and joint stiffness. After one month of treatment, his joint pains had resolved, excepting for occasional slight pain at one shoulder. This individual's problems with raising his arms above his head, driving and bending over have resolved.

It has been observed that patients treated with the preferred embodiment involving acyclovir have experienced beneficial effect approximately one week after commencement of treatment, and that resolution of pain and stiffness to the same degree as noted with the valacyclovir method is eventually achieved, albeit after a somewhat longer course of treatment. The longer treatment period may be considered an attractive tradeoff when it is taken into account that acyclovir is substantially less expensive than valacyclovir.

Example 6

A 56-year-old male presented with complaints of pain in his spine, shoulders, elbows, wrists, fingers, hips, knees, ankles, and heels. He had previously been diagnosed as having osteoarthritis. He also noted associated morning stiffness and complained of difficulty walking, climbing stairs, and with jogging. He was placed on acyclovir, L-lysine, metronidazole, and minocycline resulting in a dramatic diminution of his pain within two weeks. This patient's difficulties with walking and climbing stairs also resolved during the same two weeks. Treatment is ongoing.

Example 7

A 78-year-old male presented with complaints of pain in his cervical spine, lumbar spine and knees. This patient had also previously been diagnosed as having osteoarthritis. He noted associated morning stiffness in those areas as well as difficulty standing which particularly aggravated his lower back pain. He was treated with acyclovir, L-lysine, metronidazole, and minocycline. The treatment effected resolution of his neck and lower back pain, and his knee pain within sixty days.

Example 8

A 50-year-old male who was status post right hip replacement, secondary to avascular necrosis, presented with complaints of multiple joint pain. Evaluation determined that he was suffering from reactive arthritis. He had previously been treated with nonsteroidal anti-inflammatory inflammatory drugs. He was then started on acyclovir, 400 mg BID, L-lysine, 500 mg BID, metronidazole, 250 mg BID, and minocycline, 100 mg BID. Within three weeks this gentleman noted significant improvement in all joint symptoms. Treatment is ongoing.

Example 9

A 31-year-old male presented with complaints of shoulder, hand, knee, and foot pain. Swelling in hands was also noted. This man was unable to even jog without knee pain. Additionally, he had a positive skin test for TB. He was placed on InH, 300 QD, metronidazole, 250 mg BID, minocycline, 100 mg BID, acyclovir, 400 mg BID, L-lysine, 500 mg BID, and pyridoxine, 50 QD. Noted total resolution of all symptoms within three months. Now runs on a daily basis without pain, and actively works out in the weight room without pain. Has not experienced any interim swelling of his hands.

There have been thus described certain preferred embodiments of a method for treatment of conditions in human beings associated with either or both reactive arthritis or idiopathic bursitis. While preferred embodiments have been described and disclosed, it will be recognized by those with skill in the art that modifications are within the true scope and spirit of the invention. The appended claims are intended to cover all such modifications.

We claim:

1. A method for medically treating the symptoms of reactive arthritis or bursitis in humans comprising:
   administering to a patient an effective amount of the combination of L-lysine, minocycline hydrochloride, metronidazole, and acyclovir.

2. The treatment of claim 1 wherein:
   (A) between approximately one and approximately ten grams per day of L-lysine are administered, (B) between approximately 50 and approximately 200 milligrams per day of minocycline hydrochloride are administered, (C) between approximately 100 and approximately 1,000 milligrams per day of metronidazole are administered, and (D) administration of between approximately 200 milligrams and approximately 4 grams per day of acyclovir.

3. The treatment of claim 2 wherein:
   approximately one gram of L-lysine is administered once a day.

4. The treatment of claim 2 wherein:
   approximately 100 milligrams of said minocycline hydrochloride is administered twice daily.

5. The treatment of claim 2 wherein:
   approximately 250 milligrams of said metronidazole is administered four times a day.

6. The treatment of claim 2 wherein:
   approximately 400 milligrams of acyclovir is administered twice daily.

7. The treatment of claim 3 wherein:
   approximately 100 milligrams of said minocycline hydrochloride is administered twice daily.

8. The treatment of claim 3 wherein:
   approximately 250 milligrams of said metronidazole is administered four times a day.

9. The treatment of claim 3 wherein:
   approximately 400 milligrams of acyclovir is administered twice daily.

10. The treatment of claim 4 wherein:
    approximately 250 milligrams of said metronidazole is administered four times a day.

11. The treatment of claim 4 wherein:
    approximately 400 milligrams of acyclovir is administered twice daily.

12. The treatment of claim 5 wherein:
    approximately 400 milligrams of acyclovir is administered twice daily.

13. The treatment of claim 7 wherein:
    approximately 250 milligrams of said metronidazole is administered four times a day.

14. The treatment of claim 7 wherein:
    approximately 400 milligrams of acyclovir is administered twice daily.

15. The treatment of claim 8 wherein:
    approximately 400 milligrams of acyclovir is administered twice daily.

16. The treatment of claim 10 wherein:
    approximately 400 milligrams of acyclovir is administered twice daily.

17. The treatment of claim 13 wherein:
    approximately 400 milligrams of acyclovir is administered twice daily.

18. The treatment of claim 1 including:
    administering to a patient an effective amount of isonicotinic acid hydrazide.

19. The treatment of claim 2 including:
    administration of between approximately 50 and approximately 300 milligrams per day of isonicotinic acid hydrazide.

20. The treatment of claim 19 wherein:
    approximately 300 milligrams of said isonicotinic acid hydrazide is administered once a day.

21. The treatment of claim 3 including:
    administration of between approximately 50 and approximately 300 milligrams per day of isonicotinic acid hydrazide.

22. The treatment of claim 21 wherein:
    approximately 300 milligrams of said isonicotinic acid hydrazide is administered once a day.

23. The treatment of claim 4 including:
    administration of between approximately 50 and approximately 300 milligrams per day of isonicotinic acid hydrazide.

24. The treatment of claim 23 wherein:
    approximately 300 milligrams of said isonicotinic acid hydrazide is administered once a day.

25. The treatment of claim 5 including:
    administration of between approximately 50 and approximately 300 milligrams per day of isonicotinic acid hydrazide.

26. The treatment of claim 25 wherein:
    approximately 300 milligrams of said isonicotinic acid hydrazide is administered once a day.

27. The treatment of claim 6 including:
    administration of between approximately 50 and approximately 300 milligrams per day of isonicotinic acid hydrazide.

28. The treatment of claim 27 wherein:
    approximately 300 milligrams of said isonicotinic acid hydrazide is administered once a day.

29. The treatment of claim 7 including:
    administration of between approximately 50 and approximately 300 milligrams per day of isonicotinic acid hydrazide.

30. The treatment of claim 29 wherein:
approximately 300 milligrams of said isonicotinic acid hydrazide is administered once a day.

31. The treatment of claim 8 including:
administration of between approximately 50 and approximately 300 milligrams per day of isonicotinic acid hydrazide.

32. The treatment of claim 31 wherein:
approximately 300 milligrams of said isonicotinic acid hydrazide is administered once a day.

33. The treatment of claim 9 including:
administration of between approximately 50 and approximately 300 milligrams per day of isonicotinic acid hydrazide.

34. The treatment of claim 33 wherein:
approximately 300 milligrams of said isonicotinic acid hydrazide is administered once a day.

35. The treatment of claim 10 including:
administration of between approximately 50 and approximately 300 milligrams per day of isonicotinic acid hydrazide.

36. The treatment of claim 35 wherein:
approximately 300 milligrams of said isonicotinic acid hydrazide is administered once a day.

37. The treatment of claim 11 including:
administration of between approximately 50 and approximately 300 milligrams per day of isonicotinic acid hydrazide.

38. The treatment of claim 37 wherein:
approximately 300 milligrams of said isonicotinic acid hydrazide is administered once a day.

39. The treatment of claim 12 including:
administration of between approximately 50 and approximately 300 milligrams per day of isonicotinic acid hydrazide.

40. The treatment of claim 39 wherein:
approximately 300 milligrams of said isonicotinic acid hydrazide is administered once a day.

41. The treatment of claim 13 including:
administration of between approximately 50 and approximately 300 milligrams per day of isonicotinic acid hydrazide.

42. The treatment of claim 41 wherein:
approximately 300 milligrams of said isonicotinic acid hydrazide is administered once a day.

43. The treatment of claim 14 including:
administration of between approximately 50 and approximately 300 milligrams per day of isonicotinic acid hydrazide.

44. The treatment of claim 43 wherein:
approximately 300 milligrams of said isonicotinic acid hydrazide is administered once a day.

45. The treatment of claim 15 including:
administration of between approximately 50 and approximately 300 milligrams per day of isonicotinic acid hydrazide.

46. The treatment of claim 45 wherein:
approximately 300 milligrams of said isonicotinic acid hydrazide is administered once a day.

47. The treatment of claim 16 including:
administration of between approximately 50 and approximately 300 milligrams per day of isonicotinic acid hydrazide.

48. The treatment of claim 47 wherein:
approximately 300 milligrams of said isonicotinic acid hydrazide is administered once a day.

49. The treatment of claim 17 including:
administration of between approximately 50 and approximately 300 milligrams per day of isonicotinic acid hydrazide.

50. The treatment of claim 49 wherein:
approximately 300 milligrams of said isonicotinic acid hydrazide is administered once a day.

* * * * *